United States Patent [19]

Fujita et al.

[11] Patent Number: 5,401,434
[45] Date of Patent: Mar. 28, 1995

[54] CIS-1,4-SUBSTITUTED 2-BUTENE DERIVATIVE

[75] Inventors: Atsuko Fujita; Shuichi Matsui; Yuichi Onji; Makoto Ushioda; Yasuyuki Goto, all of Chiba, Japan

[73] Assignee: Chisso Corporation, Osaka, Japan

[21] Appl. No.: 41,198

[22] Filed: Apr. 1, 1993

[30] Foreign Application Priority Data

Apr. 3, 1992 [JP] Japan .................. 4-082208

[51] Int. Cl.⁶ .............. C09K 19/30; C09K 19/12; C09K 19/54; C07C 255/00
[52] U.S. Cl. ............... 252/299.63; 252/299.6; 252/299.5; 558/411; 558/425
[58] Field of Search .......... 252/299.63, 299.6, 299.5, 252/299.01; 558/411, 425

[56] References Cited

U.S. PATENT DOCUMENTS

| 5,032,312 | 7/1991 | Kelly ................... 252/299.01 |
| 5,055,220 | 10/1991 | Uchida et al. ........... 252/299.01 |
| 5,234,622 | 8/1993 | Funfschilling et al. .... 252/299.61 |

FOREIGN PATENT DOCUMENTS 0442306 8/1991 European Pat. Off. .
3509170 9/1986 Germany .
WO91/03450 3/1991 WIPO .

Primary Examiner—Robert L. Stoll
Assistant Examiner—C. Harris

[57] ABSTRACT

A novel liquid crystal compound having an intermediate group of a cis-1,4-substituted 2-butenyl group, low viscosity and a broad mesomorphic temperature range is provided, which compound is expressed by the following formula:

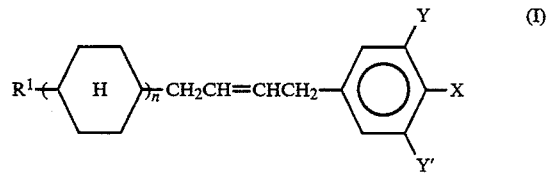

wherein $R^1$ represents an alkyl group of 1 to 10 carbon atoms, n represents 1 or 2, X represents a hydrogen atom, an alkyl group, a halogen atom, a cyano group, an alkoxy group, a methyl group substituted by 1 to 3 halogen atom(s) or a trihaloalkoxy group, and Y and Y' each independently represents a hydrogen atom, or a halogen atom.

7 Claims, No Drawings

CIS-1,4-SUBSTITUTED 2-BUTENE DERIVATIVE

BACKGROUND OF THE INVENTION

1. Field of the Invention

This invention relates to a cis-1,4-substituted 2-butene derivative useful for liquid crystal materials. More particularly, it relates to a liquid crystal compound containing a 2Z-butenyl group inside its molecule and a liquid crystal composition containing the same.

2. Description of the Related Art

Display elements making use of liquid crystals have been broadly utilized for clocks, electric computers, etc. These liquid crystal display elements utilize the optical anisotropy and dielectric anisotropy of liquid crystal substances. Liquid crystal phases include a nematic liquid crystal phase, a smectic liquid crystal phase and a cholesteric liquid crystal phase. Among these phases, display elements utilizing nematic liquid crystal have been most broadly practically used. Further, display modes applied to the liquid crystal display includes TN (twisted nematic) mode, DS (dynamic scattering) mode, guest-host mode, DAP mode, etc. Many liquid crystalline compounds including those at a studying stage have been known, but at present, there is no single substance which is sealed in a display element and used. This is because while liquid crystal substances for display elements are preferred to be those which exhibit liquid crystal phase within a temperature range as broad as possible around a room temperature at which they are most often used as display elements in the natural fields, and further they should be sufficiently stable to environmental factors and have sufficient physical properties for driving the display element, a single substance satisfying these conditions has not yet been found. Thus, at present, liquid crystal compositions having such characteristics have been prepared by mixing several kinds of liquid crystal materials or further mixing non-liquid crystalline compounds therewith. Further, these liquid crystal compositions are required to be stable to moisture, light, heat, air, etc. usually present under the environment where they are used. Further, the compositions are required to be stable to electric field and electromagnetic irradiation, and further the liquid crystal compounds to be mixed are required to be chemically stable to one another under the environment where they are used. Further, the values of various physical properties such as optical anisotropy value, dielectric anisotropy value, conductance value, etc. are required to be suitable depending on a display mode and a shape of element. In particular, the importance of a substance having a low optical anisotropy value as a material for liquid crystal display element of thin film transistor (TFT) mode is increasing. In order to meet such requirements, single liquid crystal compounds having various characteristics have been developed, and as a compound for improving the values of viscosity and optical anisotropy, compounds having flexible cross linking portions between molecules have been found. For example, the following compound A having a carbon chain in the central portion of a molecule is disclosed in Japanese patent application laid-open No. Sho 61-215336. Furthermore, West German patent application laid-open No. 4027840 discloses the following compounds B having a chain of four carbon atoms as a central group in order to make the molecular structure more flexible. Japanese patent application laid-open No. Hei 3-66632 also discloses the following compound C.

Further, as to a liquid crystalline compound having a chain of four carbon atoms including an unsaturated bond, no examples have been known except the following compound D disclosed as a synthesized intermediate compound in Japanese patent application laidopen No. Hei 3-66632. However, such substituted stylene compounds as the compound D are thermally unstable. Thus, there have not been known any liquid crystal material having a chain of four carbon atoms and unsaturated bond(s), and usable in the ordinal environment.

Compound A (Japanese patent application laid-open No. Sho 59-225129):

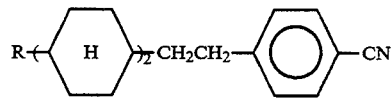

Compound B (West German patent application laid-open No. 4027840. A1):

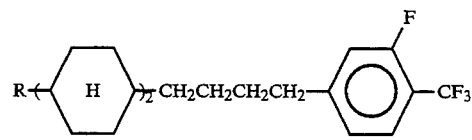

Compound C (Japanese patent application laid-open No. Hei 3-66632):

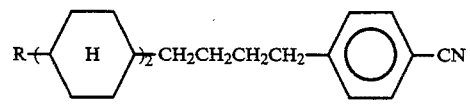

Compound D (Japanese patent application laid-open No. Hei 3-66632):

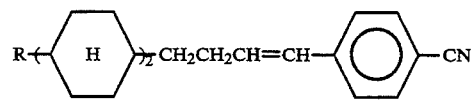

The present inventors have made extensive research in order to solve the above-mentioned problems, and as a result, have found a compound having a novel structure and having improved characteristics as compared with generally known liquid crystal compounds, and have completed the present invention, which compound is expressed by the following formula (I):

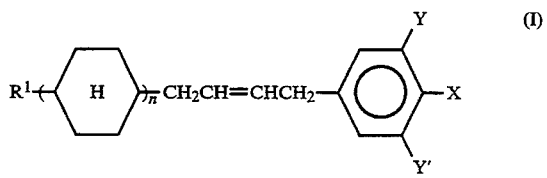

wherein $R^1$ represents an alkyl group of 1 to 10 carbon atoms; n represents 1 or 2; X represents a hydrogen atom, an alkyl group, a halogen atom, a cyano group, an alkoxy group, a methyl group substituted by 1 to 3 halogen atoms, or a trihaloalkoxy group; Y and Y' each independently represents a hydrogen atom or a halogen atom.

It has been possible to apply an unsaturated group to an intermediate group adjacent to an aromatic ring to obtain a thermally stable compound resistant to use in the ordinal environment by separating the unsaturated group by one carbon atom from an aromatic ring. Thus, the compound of the present invention has a moderately rigid and free structure as compared with known compounds to be easily oriented within a liquid crystal phase, and has a relatively high elastic constant ratio. Further, the compound of the present invention has characteristics of forming a liquid crystal phase within a broad temperature range, although it has a high flexible 1-butenyl group within a molecule, and having a moderate optical anisotropy value and a very low viscosity. Further, the compound of the present invention is stable chemically and thermally, and not degraded under conditions of electromagnetic radiation, impression of electric voltage, etc. In addition, in the case where the compound of the present invention is used as a component of a liquid crystal composition, it has a superior compatibility with other liquid crystal materials to make it possible to compose a novel liquid crystal display element having useful characteristics. Further, the compound of the present invention can vary its characteristics by modifying its ring structures and the substituents on the rings thereof. Among the compounds of the present invention, preferable ones are exemplified as follows.

A compound of the formula (I) wherein n=1, X=C$_2$H$_5$, Y=H, Y'=H:

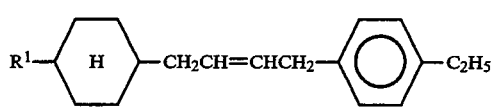
(I-a)

A compound of the formula (I) wherein n=1, X=C$_3$H$_7$, Y=H, Y'=H:

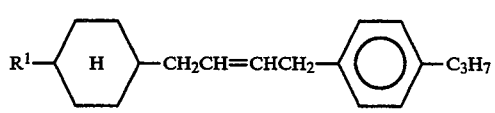
(I-b)

A compound of the formula (I) wherein n=1, X=C$_5$H$_{11}$, Y=H, Y'=H:

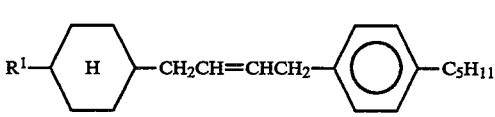
(I-c)

A compound of the formula (I) wherein n=1, X=F, Y=H, Y'=H:

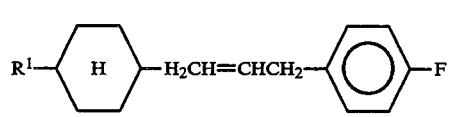
(I-d)

A compound of the formula (I) wherein n=1, X=F, Y=F, Y'=H:

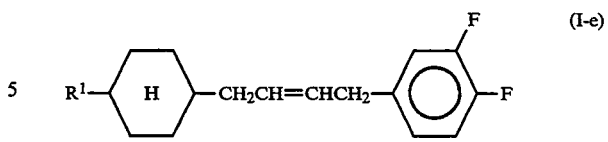
(I-e)

A compound of the formula (I) wherein n=1, X=F, Y=F, Y'=F:

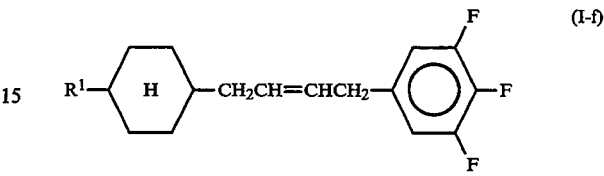
(I-f)

A compound of the formula (I) wherein n=1, X=CN, Y=H, Y'=H:

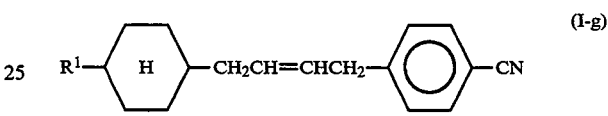
(I-g)

A compound of the formula (I) wherein n=1, X=CN, Y=F, Y'=H:

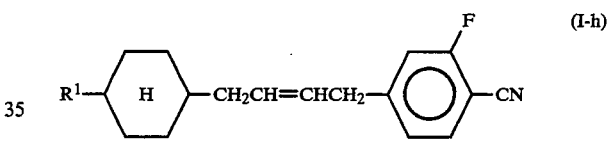
(I-h)

A compound of the formula (I) wherein n=1, X=CF$_3$, Y=H, Y'=H:

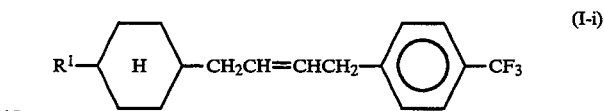
(I-i)

A compound of the formula (I) wherein n=1, X=OCF$_3$, Y=H, Y'=H:

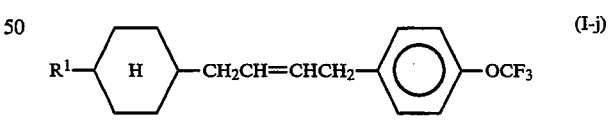
(I-j)

A compound of the formula (I) wherein n=2, X=C$_2$H$_5$, Y=H, Y'=H:

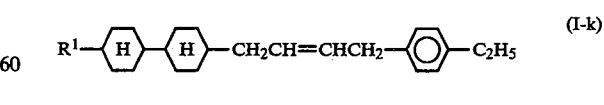
(I-k)

A compound of the formula (I) wherein n=2, X=C$_3$H$_7$, Y=H, Y'=H:

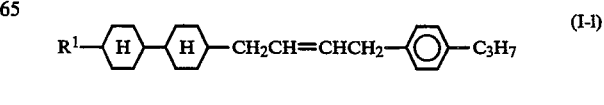
(I-l)

A compound of the formula (I) wherein n=2, X=C₅H₁₁, Y=H, Y'=H:

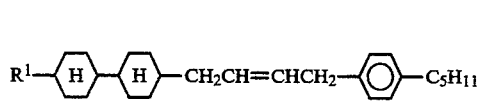

A compound of the formula (I) wherein n=2, X=F, Y=H, Y'=H:

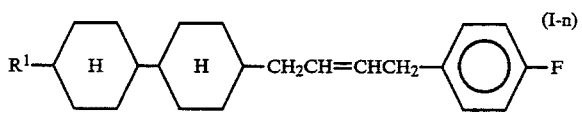

A compound of the formula (I) wherein n=2, X=F, Y=F, Y'=H:

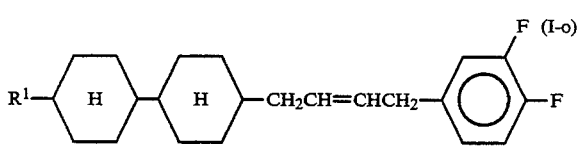

A compound of the formula (I) wherein n=2, X=F, Y=F, Y'=F:

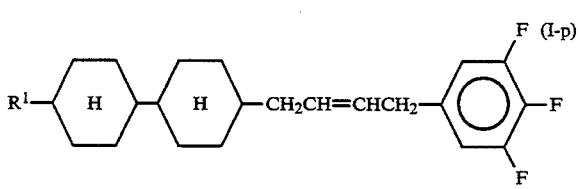

A compound of the formula (I) wherein n=2, X=CN, Y=H, Y'=H:

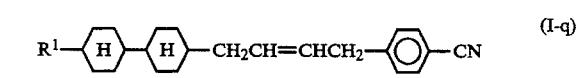

A compound of the formula (I) wherein n=2, X=CN, Y=F, Y'=H:

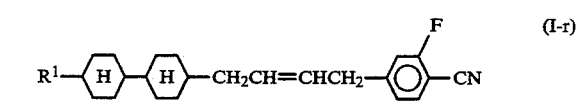

A compound of the formula (I) wherein n=2, X=CF₃, Y=H, Y'=H:

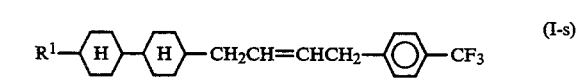

A compound of the formula (I) wherein n=2, X=OCF₃, Y=H, Y'=H:

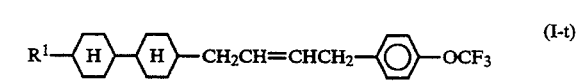

A compound of the formula (I) wherein n=2, X=OCF₃, Y=F, Y'=H:

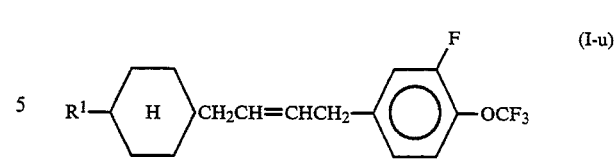

A compound of the formula (I) wherein n=2, X=OCF₃, Y=F, Y'=F:

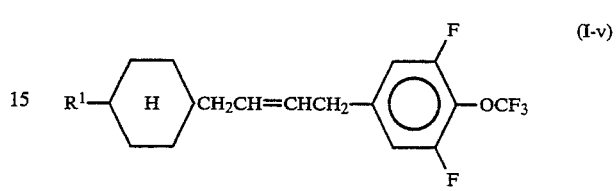

A compound of the formula (I) wherein n=2, X=OCF₃, Y=F, Y'=H:

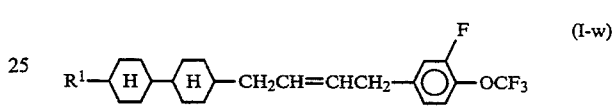

A compound of the formula (I) wherein n=2, X=OCF₃, Y=F, Y'=F:

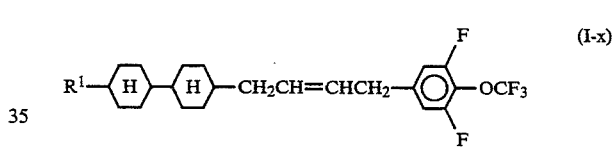

Among these compounds, those of I-g, I-h, I-q and I-r having a cyano group afford a large dipole moment, and those of I-i and I-s having a trifluoromethyl group reduce viscosity and afford a large polarizability, and thus, they are preferred. Further, among the compounds of the present invention, those having three six-membered rings within the molecule, i.e. the so-called three-rings compounds are preferable, since they can establish a liquid crystal temperature range in the vicinity of a room temperature, and broaden the temperature range.

Among the compounds of the present invention, those expressed by the formula (I) wherein R¹ represents an alkyl group of 2 to 5 carbons are preferred in that they can broaden the liquid crystal range.

The liquid crystal composition provided by the present invention is preferred to be a liquid crystal dielectric material comprising a component (A) containing at least one of compounds expressed by the formula (I), and besides, a component (B) containing at least one of compounds of a high dielectric anisotropy of preferably $\Delta\epsilon \geq 5$, a component (C) containing at least one of a low dielectric anisotropy of preferably $|\Delta\epsilon| < 5$ and a component (D) containing at least one of compounds having a clear point exceeding 80° C., and if necessary, another component (E).

Preferably compounds for the component (B) are shown below.

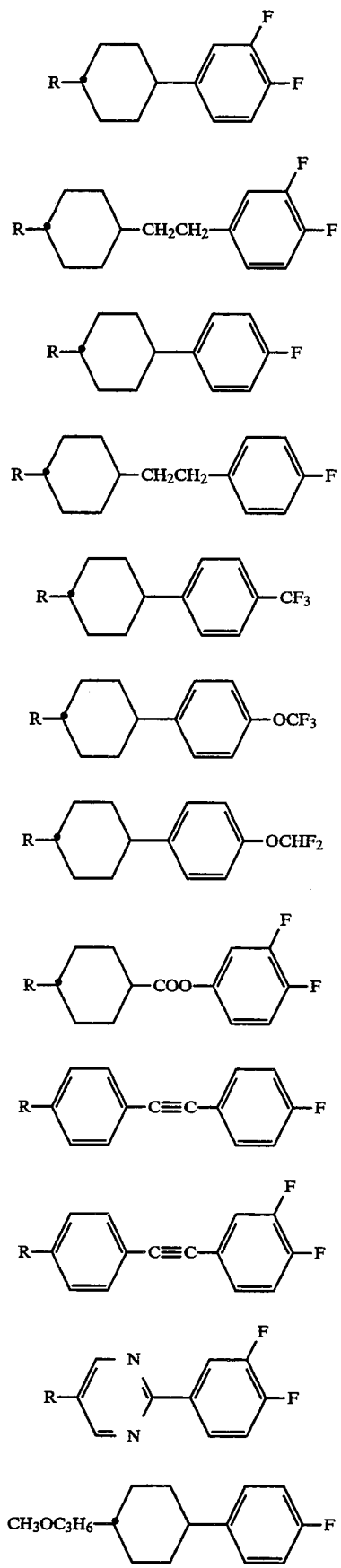
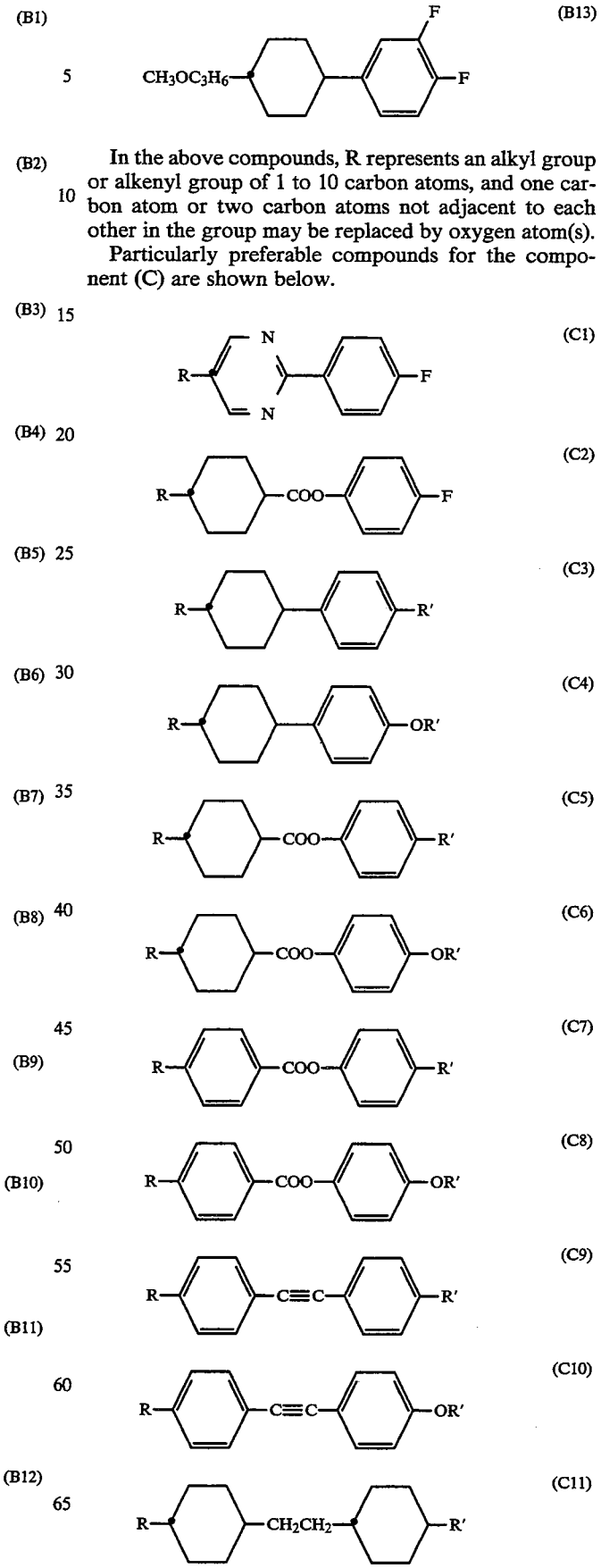
In the above compounds, R represents an alkyl group or alkenyl group of 1 to 10 carbon atoms, and one carbon atom or two carbon atoms not adjacent to each other in the group may be replaced by oxygen atom(s).
Particularly preferable compounds for the component (C) are shown below.

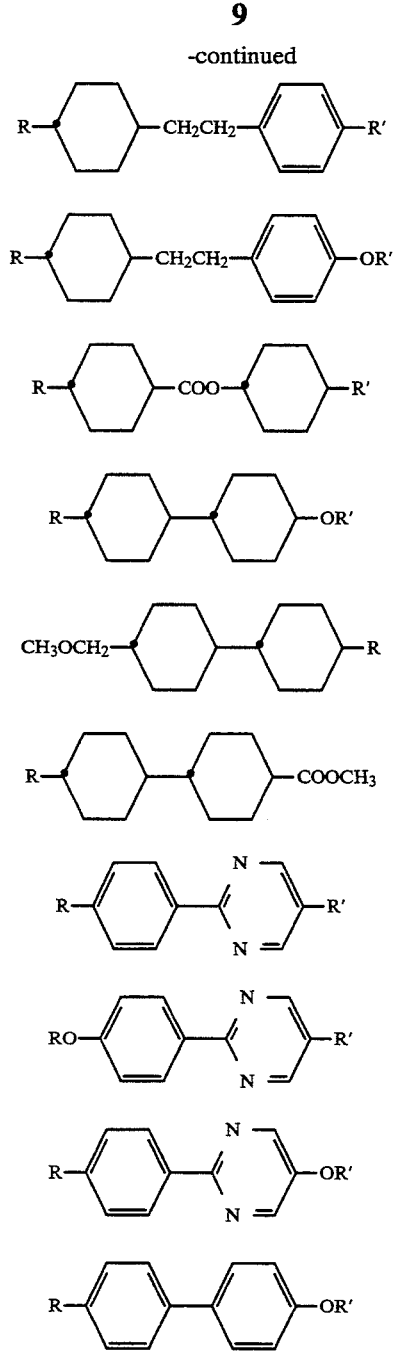
In these compounds, R and R' represent an alkyl group or alkenyl group of 1 to 10 carbon atoms, and one carbon atom or two carbon atoms not adjacent to each other in the group may be replaced by oxygen atom(s).
Particularly preferable compounds for the component (D) are shown below.
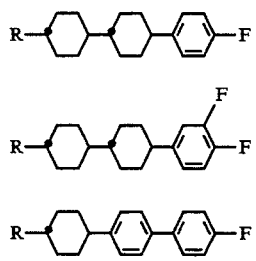
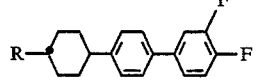
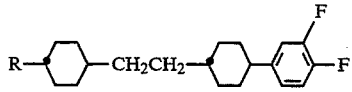
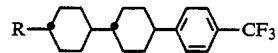
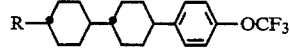
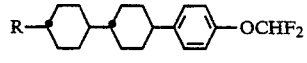
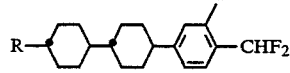
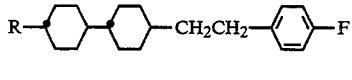
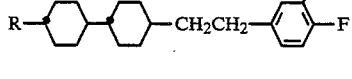
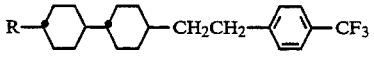
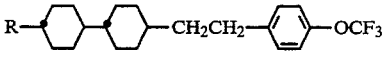
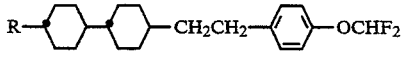
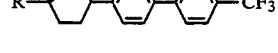
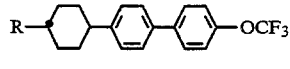
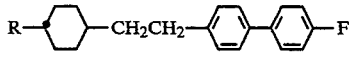
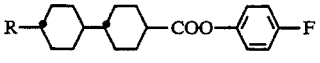
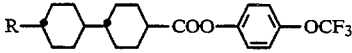
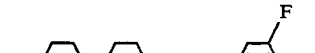

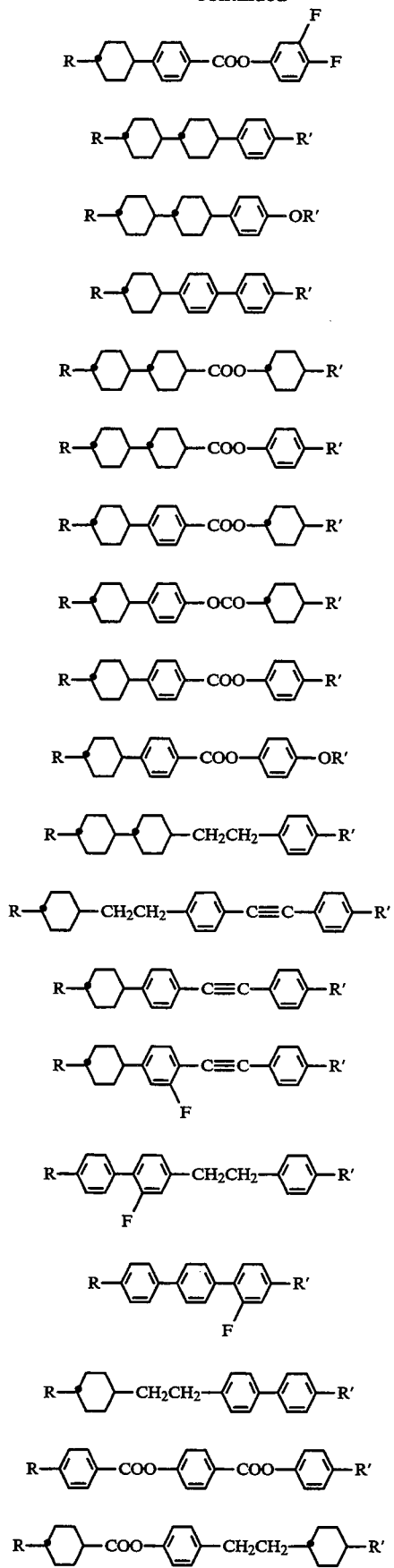
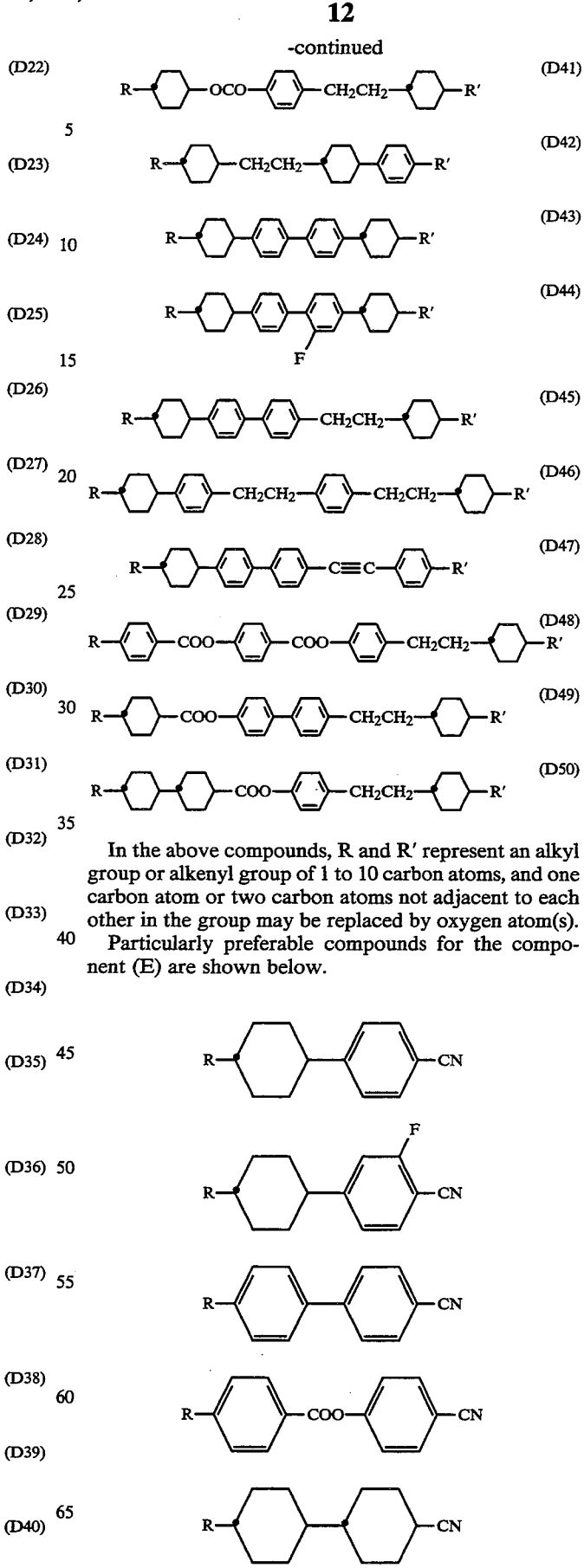
In the above compounds, R and R' represent an alkyl group or alkenyl group of 1 to 10 carbon atoms, and one carbon atom or two carbon atoms not adjacent to each other in the group may be replaced by oxygen atom(s).
Particularly preferable compounds for the component (E) are shown below.

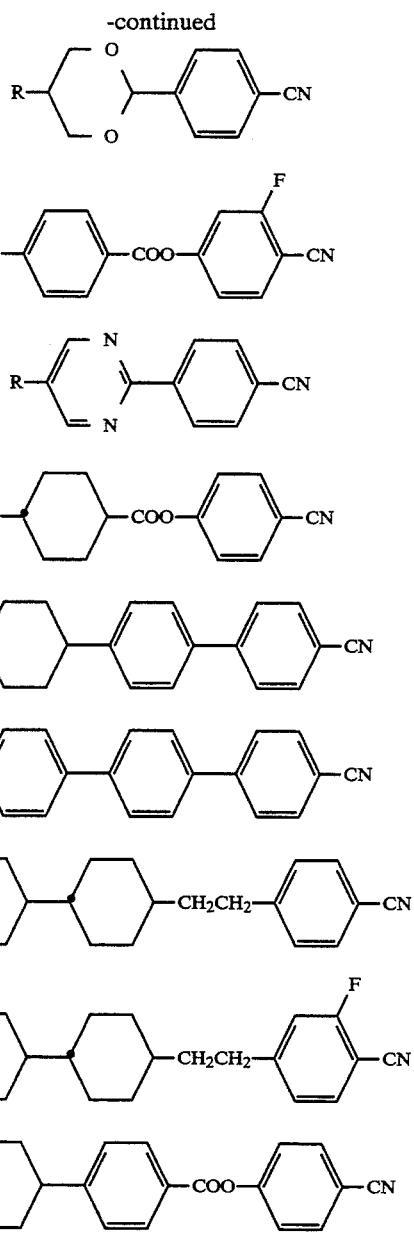
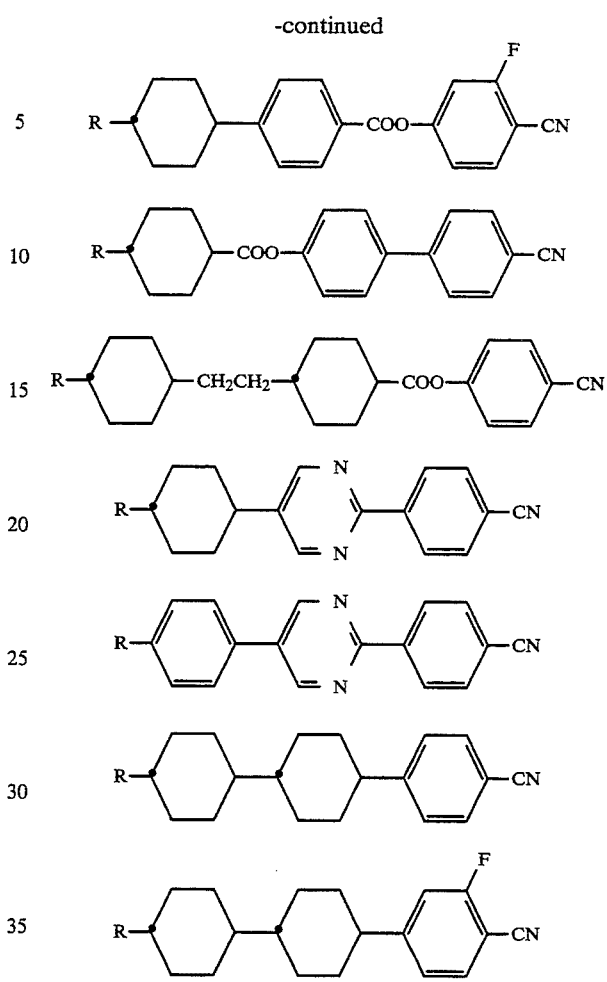

In the above compounds, R represents an alkyl group or alkenyl group of 1 to 10 carbon atoms, and one carbon atom or two carbon atoms not adjacent to each other in the group may be replaced by oxygen atom(s).

The composition according to the present invention contains at least one compound expressed by the formula (I) preferably in a proportion of 0.1 to 40% by weight, from the aspect of affording a liquid crystal having superior characteristics.

Production process

The compound of the present invention can be produced according to a reaction process shown below, for example.

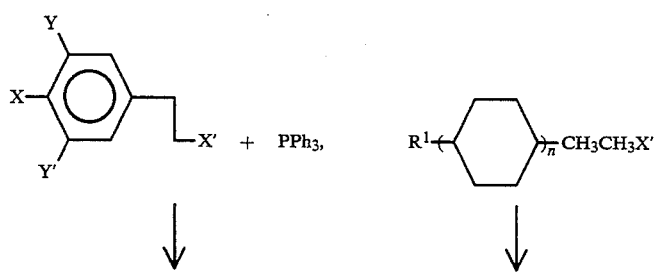

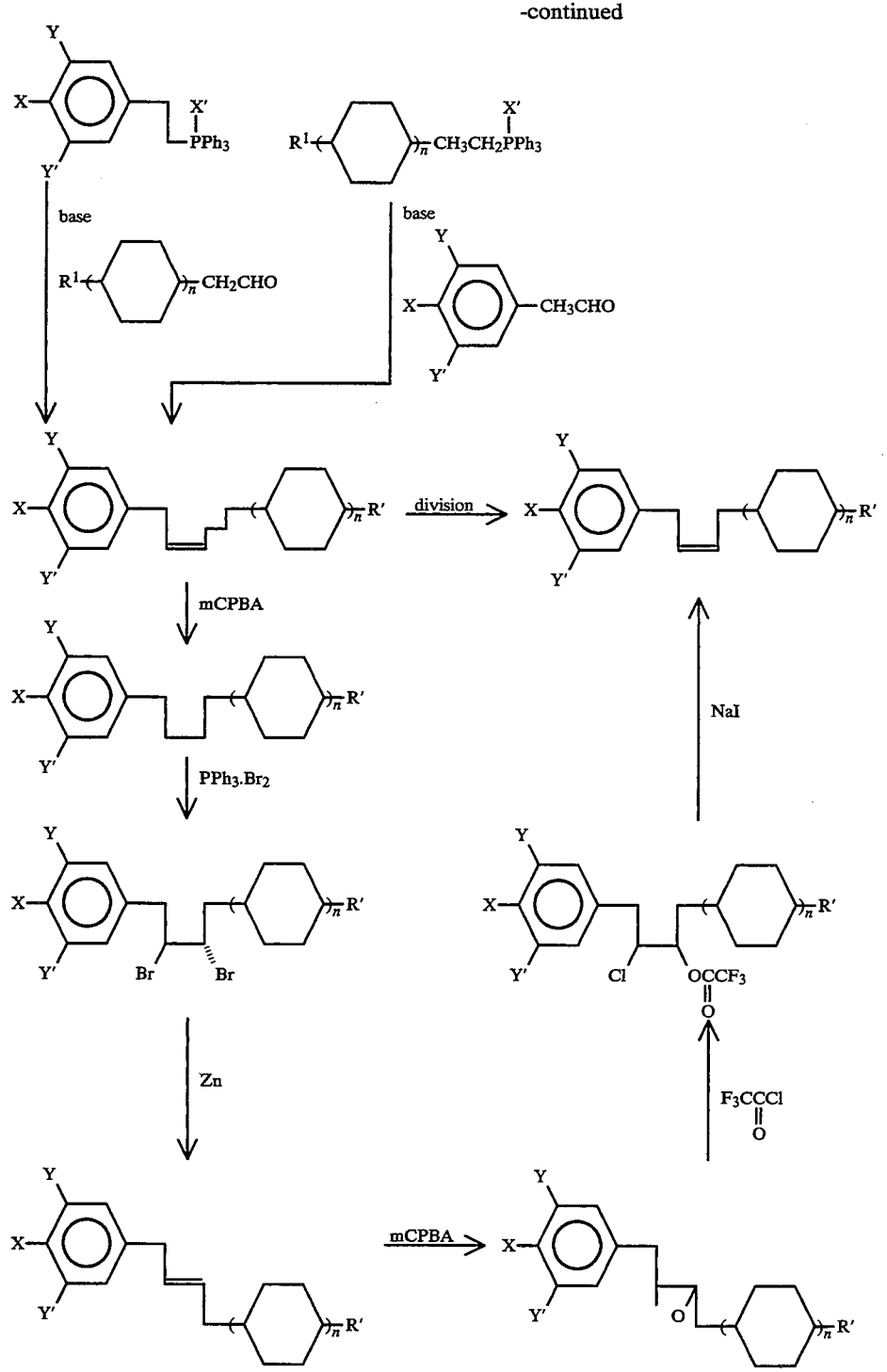
Namely, the compound of the present invention can be obtained by subjecting an aldehyde derivative expressed by the formula (II),
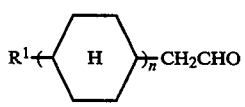
(II)
wherein $R^1$ represents an alkyl group of 1 to 10 carbon atoms, and n represents 1 or 2, and a phosphorus ylide compound expressed by the formula (III),
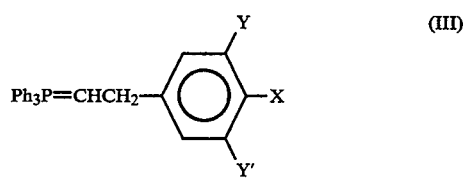
(III)

wherein X represents a hydrogen atom, an alkyl group, a halogen atom, a cyano group, an alkoxy group, a methyl group substituted by 1 to 3 halogen atom(s), or a trihaloalkoxy group, and Y and Y' represent each a hydrogen atom or a halogen atom; or an aldehyde derivative expressed by the formula (IV),

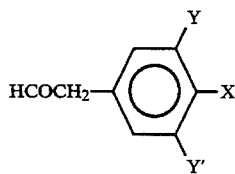

(IV)

wherein X, Y and Y' are as defined above, and a phosphorus ylide compound expressed by the formula (V),

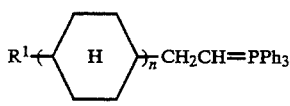

(V)

wherein R¹ and n are defined above, to a Wittig reaction described in Organic Reaction vol. 14, 270 (1965).

The compound of the present invention produced by reacting the compound of the formula (II) with the compound of the formula (III), or reacting the compound of the formula (IV) with the compound of the formula (V), is generally obtained as a mixture of its stereoisomers. The objective cis-isomer can be separated from the mixture by subjecting it to a clathrate treatment with urea, thiourea or graphite, etc. as a host molecule. Further, the stereoisomer of the compound of the present invention may be inverted to a cis-isomer according to a method disclosed in Tetrahedron Vol. 36, pp 577, if necessary. As an example of such inversion of steric structure, the following is shown. Namely, the mixture of the stereoisomers or the single stereoisomer of the compound of the present invention is subjected to bromination by using a brominating agent represented by triphenylphosphinebromine, or converted to an oxiran derivative by using a peracid, followed by bromination by using a brominating agent to obtain a 1,2-dihalogenated compound (erythrodihalogenated compound) with a high yield and a high selectivity. The thus obtained dihalogenated compound is subjected to reduction over an appropriate reducing agent, whereby it can be converted to a mixture containing the stereoisomer of the compound of the present invention in a favorable amount. Further, the stereoisomer is converted to an oxiran derivative by using a peracid, followed by reducing over hexamethyldisilane and potassium methoxide to obtain a pure compound of the present invention. Alternatively, the oxiran derivative prepared above is treated with trifluoroacetic acid halogenate to obtain a halohydrin ester, followed by reducing it over sodium iodate, to convert to a mixture containing the compound of the present invention in a favorable amount.

The reaction of the compound of the formula (II) with the compound of the formula (III), or the reaction of the compound of the formula (IV) with the compound of the formula (V), for producing the compound of the present invention, can be carried out by a known method in itself.

For example, the phosphorus ylide compound expressed by the formula (III) or (V) can be prepared from a phosphonium salt of the corresponding compound of the formula (VI),

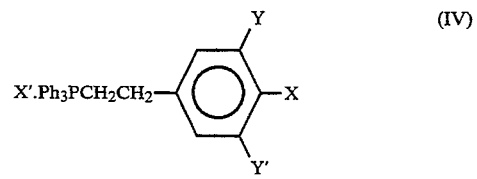

(IV)

wherein X, Y and Y' are defined as above, and X' represents a halogen atom, or the corresponding compound of the formula (VII),

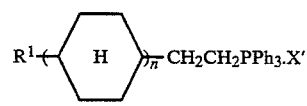

(VII)

wherein R¹ and n are mentioned above, and X' represents a halogen atom, and an appropriate base within the system. The phosphonium salt of the compound (VI) or (VII) can be easily obtained from the corresponding halogen compound and the corresponding triphenyl phosphine. The obtained phosphonium salt can be used as it is, or after purification. As a base used in generating phosphorous ylide from these phosphonium salts, potassium t-butoxide, sodium methoxide, sodium hydride, sodium dimsyl, n-butyllithium, lithium diisopropylamide, pyridine, triethylamine, etc., are exemplified. Among these bases, potassium t-butoxide, sodium methoxide, sodium hydride, sodium dimsyl and n-butyllithium are preferable, since the generated phosphorous ylide compound (III) is stable at room temperature and has a good yield. And further, potassium t-butoxide is more preferable since it is easily prepared and dealt with. The preparation of the phosphorus ylide compound (III) or (V), and the subsequent reaction with the aldehyde derivative (II) or (IV) are preferred to be carried out in a solvent, since temperature control and handling are easy. Ordinarily the preparation of phosphorus ylid compound (III) or (V) and the reaction of the generated ylid compound with the aldehyde derivative (II) or (IV) can be carried out successively in the same solvent. Although the solvent used may be sufficient unless it hinders the reaction, solvents such as diethylether, tetrahydrofuran, dioxane, benzene, toluene, xylene, hexane, heptane, dimethylsulfoxide, dimethylformamide, etc. are preferable. They are usable as a single solvent or a mixed solvent.

The thus obtained steric mixture of olefins are treated with 3 to 5 equivalents of thiourea in an appropriate solvent, whereby a complex clathrating mainly the compound of the present invention is formed. As the solvent usable, those which dissolve the compound of the present invention sufficiently and are superior in solubility with thiourea are preferred. For example, ethanol, methanol and a mixed solvent mainly of these solvents with generally used organic solvent(s) are usable. In order to isolate the compound of the present invention, it is preferred that the resulting complex is dissolved in a dilute hydrochloric acid and extracted with an appropriate solvent. The mixture consisting mainly of the compound of the present invention, obtained by the extracting process, is recrystallized from an appropriate solvent to obtain a pure compound of the present invention.

In the case where the compound of the present invention is isolated by means of column chromatography from the mixture of olefine isomers obtained as above, the isolation can be carried out by employing a combination of an appropriate adsorbent agent and solvent. As the adsorbent agent, those generally available such as silica gel, alumina and the like are usable, and the isolated compound of the present invention can be purified by general treatment like recrystallization or distillation, if necessary.

Among the compounds of the present invention, those having a cyano group at 4-position of a phenyl ring can be prepared besides the above preparing method, by reacting a compound expressed by the formula (VIII),

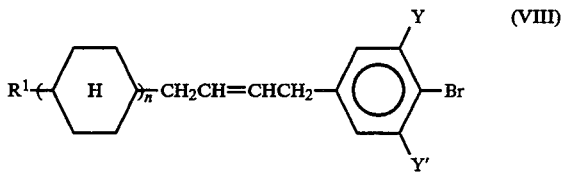

wherein $R^1$, n, Y and Y' are defined above, with an inorganic cyano compound such as copper cyanide, potassium cyanide or sodium cyanide and the like in an appropriate organic solvent. This reaction can be carried out in a polar solvent such as hexamethylphosphorictriamide, dimethylfolmamide and N-methylpyrrolidone. Although the reaction temperature can be chosen within a range of room temperature to the boiling point of the solvent, a range of 100° C. to 200° C. is preferable since the reaction proceeds rapidly. The product obtained by the reaction can be purified to a purified form.

The present invention will be described in more detail by way of example, but it should not be limited thereto.

In the following examples, the temperature properties of the mesophases are indicated by symbols N (nematic), I (istropic), S (smectic), and $C_P$=clearing point. $\epsilon_\perp$ represents a dielectric constant (perpendicular). $\Delta\epsilon$ represents a dielectric anisotropy calculated by the equation of $\Delta\epsilon - \epsilon\|| - \epsilon\perp$, $\Delta n$ represents an optical anisotropy of a liquid crystal mixture, $\eta_{20}$ represents a viscosity at 20° C., and $V_{10}$ represents a threshold voltage.

EXAMPLE 1

Preparation of 1-(4-fluorophenyl)-4-(4-pentylcyclohexyl)-2Z-butene

Into a flask, were placed triphenylphosphine (2.9 g, 11 mmol) and 4-fluorophenyl bromide (2.2 g, 11 mmol) prepared from 4-fluorophenethyl alcohol, followed by adding and dissolving xylene (5 ml), heating under reflux for 10 hours, depositing and filtering off white crystals (4.6 g, 10 mmol) of 4-fluorophenethyltriphenylphosphonium bromide. After drying, the white crystals were dissolved in tetrahydrofuran (THF, 10 ml), followed by stirring under ice cooling, adding a hexane solution (1.6M, 6.1 ml) of n-butyl lithium dropwise; stirring at room temperature for 2 hours, adding THF (5 ml) solution of 4-pentylcyclohexylacetaldehyde (2.1 g, 11 mmol), further stirring for 5 hours, adding ether after the completion of reaction. After separating the deposited white crystals by filtration, the filtrate was concentrated under reduced pressure, purifying the resulting oily substance by means of silica gel column chromatography, to obtain a mixture (2.2 g, 7.3 mmol) of 1-(4-fluorophenyl)-4-(4pentylcyclohexyl)-2Z-butene with its E-isomer.

The thus obtained mixture of isomers was dissolved in methylene chloride (20 ml), followed by adding potassium carbonate (4.1 g, 30 mmol) and metachloroperbenzoic acid (2.0 g, 12 mmol) and stirring for 8 hours, pouring the resulting mixture solution into a aqueous solution of sodium thiosulfonate after the completion of reaction, extracting the solution with methylene chloride (10 ml×3), washing the resulting organic layer with an aqueous solution (5 ml) of sodium hydrogen carbonate, further washing with water (5 ml), drying over anhydrous magnesium sulfate, and concentrating under reduced pressure to obtain 1-(4-fluorophenyl)-4-(4-pentylcyclohexyl)-2,3-butene oxide (2.3 g, 7.3 mmol). This butene oxide was dissolved in toluene (50 ml) without purification, followed by adding dibromotriphenylphosfolan (3.7 g, 8.8 mmol), heating under reflux for 3 hours, passing the reaction solution through a silica gel short column after the completion of reaction. The resulting solution was concentrated under reduced pressure, and recrystallized to form yellow oily substance from ethanol, to obtain pure 1-(4-fluorophenyl)-4-(4-pentylcyclohexyl)-erythro-2,3-dibromobutane (1.2 g, 2.6 mmol).

This erythro-dibromide was dissolved in acetic acid (50 ml), followed by adding zinc powder (0.85 g, 13 mmol) under stirring, further stirring at room temperature for two hours, adding heptane (10 ml) after the completion of reaction, filtering off insoluble substance, extracting the resulting solution with heptane (10 ml×3), washing, drying over anhydrous magnesium sulfate, concentrating under reduced pressure, and recrystallizing the resulting colorless oily substance, to obtain 1-(4-fluorophenyl)4-(4-pentylcyclohexyl)-2E-butene (750 mg, 2.5 mmol, m.p. −0.8° C.).

This substance was dissolved in methylene chloride (10 ml), followed by adding potassium carbonate (1.3 g, 9.4 mmol) and methachloroperbenzoic acid (650 mg, 3.8 mmol), stirring at room temperature for 5 hours, pouring the reaction liquid into an aqueous solution of sodium thiosulfate, extracting with methylene chloride (10 ml×3) to obtain an organic layer, washing the organic layer with a sodium hydrogen carbonate solution, washing with water, drying over anhydrous magnesium sulfate, and concentrating under reduced pressure, to obtain a colorless oily substance (oxirane derivative). Trifluoroacetic anhydride (0.86 ml) was added to a N,N-dimethylformamide (15 ml) solution of sufficiently dried lithium chloride (0.3 g), followed by stirring at room temperature for 5 minutes, dropwise-adding THF (10 ml) solution of the oxirane derivative, stirring at room temperature for 10 hours, furthermore at 50° C. for one hour, adding water (10 ml) to the reaction system after the completion of reaction, extracting with ether, drying the resulting organic layer over anhydrous magnesium sulfate, concentrating under reduced pressure, isolating and purifying the resulting brown oily substance by means of silica gel chromatography, to obtain a colorless oily substance.

This substance was dissolved in DMF (20 ml) followed by adding sodium iodide (2.3 g), stirring at 130° C. for 16 hours, adding water after the completion of reaction, extracting with heptane (30 ml×3), drying the obtained organic layer over anhydrous magnesium sulfonate, concentrating under reduced pressure, and purifying the obtained brown oily substance by means of silica gel chromatography to obtain the captioned compound (520 mg) as a colorless oil.

In the same manner as above, the following compounds are produced:
1-(4-ethylphenyl)-4-(4-ethylcyclohexyl)-2Z-butene,
1-(4-ethylphenyl)-4-(4-propylcyclohexyl)-2Z-butene,
1-(4-ethylphenyl)-4-(4-pentylcyclohexyl)-2Z-butene,
1-(4-propylphenyl)-4-(4-ethylcyclohexyl)-2Z-butene,
1-(4-propylphenyl)-4-(4-propylcyclohexyl)-2Z-butene,
1-(4-propylphenyl)-4-(4-pentylcyclohexyl)-2Z-butene,
1-(4-pentylphenyl)-4-(4-ethylcyclohexyl)-2Z-butene,
1-(4-pentylphenyl)-4-(4-propylcyclohexyl)-2Z-butene,
1-(4-pentylphenyl)-4-(4-pentylcyclohexyl)-2Z-butene,
1-(4-fluorophenyl)-4-(4-ethylcyclohexyl)-2Z-butene,
1-(4-fluorophenyl)-4-(4-propylcyclohexyl)-2Z-butene,
1-(3,4-difluorophenyl)-4-(4-ethylcyclohexyl)-2Z-butene,
1-(3,4-difluorophenyl)-4-(4-propylcyclohexyl)-2Z-butene,
1-(3,4-difluorophenyl)-4-(4-pentylcyclohexyl)-2Z-butene.

EXAMPLE 2

Preparation of
1-(3,4,5-trifluorophenyl)-4-(4-pentylcyclohexyl)-2Z-butene

Into a flask, were placed triphenylphosphine (2.9 g, 11 mmol) and 3,4,5-trifluorophenethylbromide (2.6 g, 11 mmol) prepared from 3,4,5-trifluorophenethyl alcohol, followed by adding and dissolving xylene (5 ml), heating under reflux for 10 hours, standing to cool to 80° C., adding tetrahydrofuran (THF, 10 ml) and stirring to be homogenious, ice-cooling the reaction solution, adding a hexane solution of n-butyl-lithium (1.6M, 6.1 ml) dropwise, further stirring the solution at room temperature for 2 hours after the completion of dropping, adding THF (5 ml) solution of 4-ethylcyclohexylacetaldehyde (1.7 g, 11 mmol), stirring for 5 hours, adding ether after the completion of reaction, filtering off the deposited white solid, concentrating the filtrate under reduced pressure, purifying the obtained brown oil by means of silica gel chromatography, to obtain a mixture of 1-(3,4,5-trifluorophenyl)-4-(4-pentylcyclohexyl)-2Z-butene with its E-isomer.

The obtained mixture of isomers (2.2 g, 7.3 mmol) was dissolved in methylene chloride (20 ml), followed by adding potassium carbonate (4.1 g, 30 mmol) and metachloro perbenzoic acid (2.0 g, 12 mmol), stirring for 8 hours, pouring the resulting mixed solution into an aqueous solution of sodium thiosulfate after the completion of reaction, extracting with methylene chloride (10 ml×3), washing the resulting organic layer with an aqueous solution of sodium hydrogen carbonate (5 ml), washing with water, drying over magnesium sulfate, and concentrating the resulting solution under reduced pressure, to obtain 1-(3,4,5-trifluorophenyl)-4-(4-ethylcyclohexyl)-2,3-butene oxide.

This butene oxide (2.3 g, 7.3 mmol) was dissolved in toluene (50 ml) without purification, followed by adding dibromotriphenylphosphorene (3.7 g, 8.8 mmol) and heating under reflux for 3 hours, passing the reaction liquid through a silica gel short column after the completion of reaction, concentrating under reduced pressure, and recrystalizing the obtained yellow oily substance from ethanol, to obtain 1-(3,4,5-trifluorophenyl)-4-(4-ethylcyclohexyl)-erythro-2,3-dibromobutane in a pure form.

This erythro-dibromide (1.2 g, 2.6 mmol) was dissolved in acetic acid (50 ml), followed by adding zinc powder (0.85 g, 13 mmol) under stirring, further stirring at room temperature for two hours, adding heptane (10 ml×3) after the completion of reaction, filtering off insoluble substance, extracting the resulting solution with heptane (10 ml), washing with water, drying over anhydrous magnesium sulfate, concentrating under reduced pressure, and isolating and purifying the resulting oil by means of silica gel chlomatography, to obtain a mixture of the captioned compound with its E-isomer as a colorless oil.

This substance was dissolved in methylenechloride (10 ml), followed by adding potassium carbonate (1.3 g, 9.4 mmol) and methachloroperbenzoic acid (656 mg, 3.8 mmol), agitating at room temperature for 5 hours, pouring the reaction liquid into an aqueous solution of sodium thiosulfate, extracting with methylene chloride (10 ml×3), washing the obtained organic layer with a sodium hydrogen carbonate solution, washing with water, drying over anhydrous magnesium sulfate, and concentrating under reduced pressure, to obtain a colorless oil (oxirane derivative). Trifluoroacetic anhydride (0.86 ml) was added to a N,N-dimethylformamide (15 ml) solution of sufficiently dried lithium chloride (0.3 g), followed by stirring at room temperature for 5 minutes, dropwise-adding THF (10 ml) solution of the oxirane derivative, stirring at room temperature for 10 hours, further stirring at 50° C. for one hour, adding water (10 ml) to the reaction system after the completion of reaction, extracting with ether, drying the resulting organic layer over anhydrous magnesium sulfate, concentrating under reduced pressure, isolating and purifying the resulting brown oil by means of silica gel chromatography, to obtain a colorless oil This substance was dissolved in DMF (20 ml), followed by adding sodium iodide (2.3 g), stirring at 130° C. for 16 hours, adding water after the completion of reaction, extracting with heptane (30 ml ×3) drying the obtained organic layer over anhydrous magnesium sulfate, concentrating under reduced pressure, and purifying the obtained brown oil by means of silica gel chromatography, to obtain the captioned compound (520 mg) as a colorless oil.

In the same manner as above, the following compounds are prepared.
1-(3,4,5-trifluorophenyl)-4-(4-ethylcyclohexyl)-2Z-butene,
1-(3,4,5-trifluorophenyl)-4-(4-propylcyclohexyl)-2Z-butene,
1-(4-trifluoromethylphenyl)-4-(4-ethylcyclohexyl)-2Z-butene,
1-(4-trifluoromethylphenyl)-4-(4-propylcyclohexyl)-2Z-butene,
1-(4-trifluoromethylphenyl)-4-(4-pentylcyclohexyl)-2Z-butene,
1-(4-trifluoromethoxyphenyl)-4-(4-ethylcyclohexyl)-2Z-butene,
1-(4-trifluoromethoxyphenyl)-4-(4-propylcyclohexyl)-2Z-butene,
1-(4-trifluoromethoxyphenyl)-4-(4-pentylcyclohexyl)-2Z-butene.

EXAMPLE 3

Preparation of
1-(4-propylphenyl)-4-(4-pentylcyclohexyl)cyclohexyl)-2Z-butene

Into a flask, were placed triphenylphosphine (2.3 g, 8.8 mmol) and 4-propylphenethylbromide (2.0 g, 8.8 mmol) prepared from 4-propylphenethyl alcohol, followed by adding and dissolving xylene (10 ml), heating under reflux for 10 hours, filtering off white crystals of 4-propylphenethyltriphenylphosphoniumbromide deposited after the completion of reaction, drying the obtained white crystals (4.3 g, 8.8 mmol), dissolving the white crystals in THF (10 ml), stirring under ice cooling, adding potassium-t-butoxide (984 mg, 8.8 mmol) to the reaction solution slowly, stirring the solution at room temperature for 2 hours after the completion of dropping, adding a THF solution of 4-(4-pentylcyclohexyl)cyclohexylacetoaldehyde (2.45 g, 8.8 mmol), further stirring for 5 hours, adding ether after completion of reaction, filtering off white solid deposited, concentrating the filtrate under reduced pressure, and purifying the obtained brown oil by means of silica gel column chromatography, to obtain a mixture (1.8 g, 4.4 mmol) of 1-(4-propylphenyl)-4-(4-(4-pentylcyclohexyl)-cyclohexyl)-2Z-butene and its E-isomer.

The obtained mixture of isomers was dissolved in ethanol (50 ml), followed by adding thiourea (8.0 g), stirring at room temperature for 20 hours, filtering off crystals deposited from the system after the completion of stirring, washing the obtained crystals with heptane, adding dilute hydrochloric acid (200 ml) and ether (50 ml), and stirring till the crystals dissolved therein, extracting with ether (20 ml×2), washing the obtained organic layer with water, drying over anhydrous magnesium sulfate, concentrating under reduced pressure, and recrystallizing the obtained colorless oil from ethanol, to obtain the captioned compound (0.7 g, 1.7 mmol). The phase transition temperature of this compound is shown below:

C—N 31.3° C. N—I 79.8° C.

In the same manner as above, the following compounds are prepared.
1-(4-ethylphenyl)-4-(4-(-4-ethylcyclohexyl)cyclohexyl)-2Z-butene,
1-(4-ethylphenyl)-4-(4-(-4-propylcyclohexyl)cyclohexyl)-2Z-butene,
1-(4-ethylphenyl)-4-(4-(-4-pentylcyclohexyl)cyclohexyl)-2Z-butene,
1-(4-propylphenyl)-4-(4-(-4-ethylcyclohexyl)cyclohexyl)-2Z-butene,
1-(4-propylphenyl)-4-(4-(-4-propylcyclohexyl)cyclohexyl)-2Z-butene,
1-(4-pentylphenyl)-4-(4-(-4-ethylcyclohexyl)cyclohexyl)-2Z-butene,
1-(4-pentylphenyl)-4-(4-(-4-propylcyclohexyl)cyclohexyl)-2Z-butene,
1-(4-pentylphenyl)-4-(4-(-4-pentylcyclohexyl)cyclohexyl)-2Z-butene.

EXAMPLE 4

Preparation of
1-(4-fluorophenyl)-4-(4-(-4-pentylcyclohexyl)cyclohexyl)-2Z-benzene 4-fluorophenethyltriphenylphosphoniumbromide (4.2 g, 9 mmol) was dried and then dissolved in THF (10 ml), followed by stirring under ice cooling, adding potassium-t-butoxide (1.0 g, 9 mmol) slowly to the obtained reaction solution, stirring at room temperature for 2 hours after the completion of dropping, adding a THF (50 ml) solution of 4-(4-pentylcyclohexyl)-cyclohexylacetoaldehyde (2.7 g, 9.7 mmol) and further stirring for 5 hours, adding ether after the completion of reaction, filtering off the obtained white crystals deposited, concentrating the filtrate under reduced pressure, and purifying the obtained brown oil by means of silica gel column chromatography, to obtain a mixture (2.0 g, 5.2 mmol) of 1-(4-fluorophenyl)-4-(4-(4-pentylcyclohexyl)cyclohexyl)-2Z-butene with its E-isomer.

The obtained mixture of isomers was dissolved in ethanol (100 ml), followed by adding thiourea (6.5 g), stirring at room temperature for 20 hours, filtering off crystals deposited from the system after the completion of stirring, washing the obtained crystals with heptane, adding dilute hydrochloric acid (100 ml) and ether (50 ml) and stirring till the crystals dissolved therein, extracting with ether (30 ml×3), washing the obtained organic layer with water, drying over anhydrous magnesium sulfate, concentrating under reduced pressure, and recrystallizing the obtained colorless oil from ethanol, to obtain the captioned compound (1.0 g, 2.6 mmol). The phase transition temperature of this compound is shown below:

$S_B$—N 60.2° C. N—I 65.0° C.

In the same manner as above, the following compounds are prepared.
1-(4-fluorophenyl)-4-(4-(4-ethylcyclohexyl)cyclohexyl)-2Z-butene,
1-(4-fluorophenyl)-4-(4-(4-propylcyclohexyl)cyclohexyl)-2Z-butene,
1-(3,4-difluorophenyl)-4-(4-(4-ethylcyclohexyl)cyclohexyl)-2Z-butene,
1-(3,4-difluorophenyl)-4-(4-(4-propylcyclohexyl)cyclohexyl)-2Z-butene,
1-(3,4-difluorophenyl)-4-(4-(4-pentylcyclohexyl)cyclohexyl)-2Z-butene.

$S_B$—N 51.5° C. N—I 55.2° C.

1-(3,4,5-trifluorophenyl)-4-(4-(4-ethylcyclohexyl)cyclohexyl)-2Z-butene.
1-(3,4,5-trifluorophenyl)-4-(4-(4-propylcyclohexyl)cyclohexyl)-2Z-butene.
1-(3,4,5-trifluorophenyl)-4-(4-(4-pentylcyclohexyl)cyclohexyl)-2Z-butene.

EXAMPLE 5

Preparation of
1-(4-trifluoromethylphenyl)-4-(4-(4-ethylcyclohexyl)-cyclohexyl)-2Z-butene Into a flask, were placed triphenylphosphine (2.6 g, 10 mmol) and 4-trifluoromethylphenyethylbromide (2.5 g, 10 mmol) prepared from 4-trifluoromethylphenethylalcohol, followed by adding and dissolving xylene (10 ml), heating under reflux for 10 hours, filtering off the deposited white crystals of 4-trifluoromethylphenethyltriphenylphosphoniumbromide after the completion of reaction, and drying the white crystals (4.6 g, 9 mmol). The white crystals were dissolved into THF (20 ml), followed by stirring under ice cooling, adding pottasium t-butoxid (1.0 g) dropwise into the reaction solution, stirring the solution at room temperature for 2 hours after the completion of dropping, adding THF (10 ml) solution of 4-(4-ethylcyclohexyl)cyclohexylacetoaldehyde (2.1 g, 9 mmol), further stirring for 5 hours, adding ether after the completion of reaction, filtrating off white solid deposited, concentrating the resultant filtrate under reduced pressure, and purifying the obtained brown oil by means of silica gel chromatography, to obtain a mixture of 1-(4-trifluoromethylphenyl)-4-(4-(4-ethylcyclohexyl)cyclohexyl)-2Z-butene with its E-isomer.

The obtained mixture of isomers (1.6 g, 4.1 mmol) was dissolved in ethanol (50 ml), followed by adding thiourea (7 g) and agitating at room temperature for 20 hours, filtering off the deposited crystals from the system after the completion of stirring, washing the obtained crystals with heptane, adding dilute hydrochloric acid (100 ml) and ether (30 ml), stirring till they were dissolved, extracting with ether (20 ml×3), washing the resulting organic layer with water, drying over anhydrous magnesium sulfate, concentrating under reduced pressure, and recrystallizing the obtained colorless oil from ethanol, to obtain the captioned compound (520 mg) as a white solid.

In the same manner as above, the following compounds is prepared.

1-(4-trifluoromethylphenyl)-4-(4-(4-propylcyclohexyl)-cyclohexyl)-2Z-butene,
1-(4-trifluoromethylphenyl)-4-(4-(4-pentylcyclohexyl)-cyclohexyl)-2Z-butene,
1-(4-trifluoromethoxyphenyl)-4-(4-(4-ethylcyclohexyl)-cyclohexyl)-2Z-butene,
1-(4-trifluoromethoxyphenyl)-4-(4-(4-propylcyclohexyl)cyclohexyl)-2Z-butene.
1-(4-trifluoromethoxyphenyl)-4-(4-(4-pentylcyclohexyl)cyclohexyl)-2Z-butene.

EXAMPLE 6

Preparation of 1-(4-cyanophenyl)-4-(4-(4-propylcyclohexyl)cyclohexyl)-2Z-butene

Into a flask, were placed triphenylphosphite (2.6 g, 10 mmol) and 4-bromophenethylbromide (2.6 g, 10 mmol) prepared from 4-bromophenethylalcohol, followed by adding and dissolving xylene (10 ml), heating under reflex for 10 hours after the completion of reaction, filtering off the deposited white crystals of 4-bromophenethyltriphenylphosphoniumbromide, and drying the white crystals (5.1 g, 9.5 mmol). The obtained white crystals were dissolved into THF (30 ml), followed by stirring under ice cooling, adding potassium-t-butoxid (1 g, 9 mmol) slowly into the reaction solution, stirring the solution at room temperature for 2 hours after the completion of dropping, adding THF (20 ml) solution of 4-(4-propylcyclohexyl)cyclohexylacetaldehyde (2.2 g, 9 mmol), further stirring for 5 hours, adding ether after the completion of reaction, filtrating off white solid deposited, concentrating the filtrate under reduced pressure, purifying the obtained brown oil by means of silica gel chromatography, to obtain a mixture (2.2 g, 5.3 mmol) of 1-(4-bromophenyl)-4-(4-(4-propylcyclohexyl)cyclohexyl-2Z-butene with its E-isomer.

The obtained mixture of isomers was dissolved in ethanol (50 ml), followed by adding thiourea (6.0 g), stirring at room temperature for 20 hours, filtering off crystals deposited from the system after the completion of stirring, washing the obtained crystals with heptane, adding dilute hydrochloric acid (80 ml) and ether (20 ml), stirring till they were dissolved, extracting with ether (20 ml×3), washing the obtained organic layer with water, drying over anhydrous magnesium sulfate, concentrating under reduced pressure, and recrystallizing the obtained colorless oil from ethanol, to obtain a single isomer, 1-(4-bromophenyl)-4-(4-(4-propylcyclohexyl)cyclohexyl)-2Z-butene (1.7 g, 4 mmol, N—I 60.2° C.).

The obtained pure butene derivatives of Z type was dissolved in N-methylpyrrolidone (NMP) (15 ml), followed by adding copper cyanide (0.7 g) and heating under reflux for 10 hours, adding an aqueous solution of iron chloride (1.3 g) and hydrochloric acid (3 ml) to the reaction solution, stirring at 80° C. for 2 hours, extracting with toluene (20 ml×3), washing the resulting organic layer with water, drying over anhydrous magnesium sulfate, concentrating under reduced pressure, isolating and purifying the resulting brown oil by means of silica gel chromatography, and recrystallizing from ethanol, to obtain the pure captioned compound (400 mg, 1.1 mmol). The phase transition temperature of this compound is shown below:

$S_B$—N 34.4° C. N—I 86.5°–89.0° C.

In the same manner as above, the following compounds are prepared.

1-(4-cyanophenyl)-4-(4-(4-ethylcyclohexyl)cyclohexyl-2Z-butene,
1-(4-cyanophenyl)-4-(4-(4-pentylcyclohexyl)cyclohexyl-2Z-butene,
1-(4-cyanophenyl)-4-(4-ethylcyclohexyl)-2Z-butene,
1-(4-cyanophenyl)-4-(4-propylcyclohexyl)-2Z-butene,
1-(4-cyanophenyl)-4-(4-pentylcyclohexyl)-2Z-butene.

EXAMPLE 7

Preparation of 1-(3-fluoro-4-cyanophenyl)-4-(4-(4-ethylcyclohexyl)cyclohexyl-2Z-butene Into a flask, were placed triphenylphosphine (2.9 g, 11 mmol) and 3-fluoro-4-bromophenethylbromide (2.2 g, 11 mmol) prepared from 3-fluoro-4-bromophenethylalcohol, followed by adding and dissolving xylene (15 ml), heating under reflux for 10 hours, adding THF (10 ml) to the reaction solution and stirring under ice-cooling, adding potassium-t-butoxid (1.1 g, 10 mmol) slowly to the reaction solution, stirring the reaction solution after the completion of dropping at room temperature for 2 hours, adding THF (10 ml) solution of 4-(ethylcyclohexyl) cyclohexylacetoaldehyde (2.4 g, 10 mmol), further stirring for 5 hours, adding ether after the completion of reaction, filtering off white solid deposited, concentrating the filtrate under reduced pressure, purifying the obtained brown oil by means of silica gel chromatography, to obtain a mixture (1.8 g, 4.2 mmol) of 1-(3-fluoro-4-bromophenyl)-4-(4-(4-ethylcyclohexyl)cyclohexyl)-2-Z-butene with its E-isomer.

The obtained mixture of isomers was dissolved in ethanol (50 ml), followed by adding thiourea (7.5 g), agitating at room temperature for 20 hours, filtering off crystals deposited from the system after the completion of stirring, washing the obtained crystals with heptane, adding dilute hydrochloric acid (100 ml) and ether (30 ml), stirring till they were dissolved, extracting with ether (30 ml×3), washing the obtained organic layer with water, drying over anhydrous magnesium sulfate, concentrating under reduced pressure, and recrystalizing the obtained colorless oil from ethanol, to obtain the pure isomer of 1-(3-fluoro-4-cyanophenyl)-4-(4-(4-propylcyclohexyl)cyclohexyl)-2z-butene (0.8 g, 1.9 mmol).

The obtained pure butene derivative of z type was dissolved in NMP (8 ml), followed by adding copper cyanide (0.8 g) and heating under reflex for 10 hours, after the completion of reaction, adding an aqueous solution (15 ml) of iron chloride (0.65 g) and hydrochloric acid (1.5 ml) after the completion of stirring, stirring at 80° C. for 2 hours, extracting with toluene (20 ml×3), washing the obtained organic layer with water, drying over anhydrous magnesium sulfate, concentrating under reduced pressure, isolating and purifying the resulting brown oil by means of silica gel chromatography, and recrystalizing the obtained substance from ethanol, to obtain the pure captioned compound as white solid.

In the same manner as above, the following compounds are prepared.
1-(3-fluoro-4-cyanophenyl)-4-(4-(4-ethylcyclohexyl)cyclohexyl)-2Z-butene,
1-(3-fluoro-4-cyanophenyl)-4-(4-(4-pentylcyclohexyl)cyclohexyl)-2Z-butene,
1-(3-fluoro-4-cyanophenyl)-4-(4-ethylcyclohexyl)cyclohexyl)-2Z-butene,
1-(3-fluoro-4-cyanophenyl)-4-(4-propylcyclohexyl)cyclohexyl)-2Z-butene,
1-(3-fluoro-4-cyanophenyl)-4-(4-pentylcyclohexyl)cyclohexyl)-2Z-butene,

EXAMPLE 8

Preparation
1-(3-fluoro-4-trifluoromethoxypenyl)-4-(4-(4-ethylcyclohexyl)cyclohexyl)-2Z-butene Into a flask, were placed triphenylphosphine (2.9 g, 10 mmol) and 3-fluoro-4-trifluoromethoxyphenetylbromide prepared from 3-fluoro-4-trifluoromethoxyphenethylalcohol, followed by adding and dissolving xylene (10 ml), heating under reflux for 10 hours, standing to cool to 80° C., adding THF (20 ml) to the reaction solution and stirring to be homogeneous, ice-cooling the reaction solution, adding potassium-t-butoxid (1.0 g) slowly stirring the solution at room temperature for 2 hours after the completion of dropping, adding THF (10 ml) solution of 4-(4-ethylcyclohexyl)cyclohexylacetaldehyde (2.6 g, 9.1 mmol), further stirring 5 hours, adding ether after the completion of reaction, filtering off white solid deposited, concentrating the resultant filtrate under reduced pressure, purifying the obtained brown oil by means of silica gel chromatography, to obtain a mixture of 1-(3-fluoro-4-trifluoromethoxyphenyl)-4-(4-(4-ethylcyclohexyl)cyclohexyl)-2Z-butene with its with its E-isomer.

The obtained mixture of isomers (1.75 g, 4.1 mmol) was dissolved in ethanol (50 ml), followed by adding thiourea (7 g) and stirring at room temperature for 20 hours, filtrating deposited crystal from the system after the completion of stirring, washing the obtained crystal with heptane, adding dilute hydrochloric acid (100 ml) and ether (30 ml×3), stirring till they were dissolved, extracting with ether (20 ml), washing the resulting organic layer with water, drying over anhydrous magnesium sulfate, concentrating under reduced pressure, and recrystalizing the obtained colorless oil from ethanol, to obtain the captioned compound as a white solid.

In the same manner as above, the following compounds are prepared.
1-(3-fluoro-4-trifluoromethoxyphenyl)-4-(4-(4-propylcyclohexyl)cyclohexyl)-2Z-butene,
1-(3-fluoro-4-trifluoromethoxyphenyl)-4-(4-(4-pentylcyclohexyl)cyclohexyl)-2Z-butene,
1-(3-fluoro-4-trifluoromethoxyphenyl)-4-(4-ethylcyclohexyl)cyclohexyl)-2Z-butene,
1-(3-fluoro-4-trifluoromethoxyphenyl)-4-(4-propylcyclohexyl)cyclohexyl-2Z-butene,
1-(3-fluoro-4-trifluoromethoxyphenyl)-4-(4-pentylcyclohexyl)cyclohexyl)-2Z-butene,
1-(3,5-difluoro-4-trifluoromethoxyphenyl)-4-(4-ethylcyclohexyl)cyclohexyl)-2Z-butene,
1-(3,5-difluoro-4-trifluoromethoxyphenyl)-4-(4-propylcyclohexyl)cyclohexyl)-2Z-butene,
1-(3,5-difluoro-4-trifluoromethoxyphenyl)-4-(4-pentylcyclohexyl)cyclohexyl)-2Z-butene.

EXAMPLE A 1-(3,4-fluorophenyl)-4-(4-(4-pentylcyclohexyl)cyclohexyl)-2Z-butene (15%) of the compound of the present invention was mixed with the following liquid crystal composition, ZLI-1132 made by Merk Co., Ltd.:

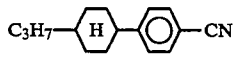  24 parts by weight

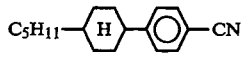  36 parts by weight

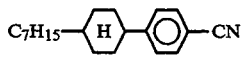  25 parts by weight

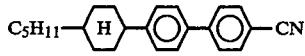  15 parts by weight and the physical properties of the resulting composition were measured. The results were as follows:
$C_P$ (°C.)=73.4, $\Delta\epsilon$=9.9, $\epsilon\perp$=4.3, $\Delta n$=0.125, $\eta_{20}$=26.9, $V_{10}$=1.66.

Further, when this composition was allowed to stand in a freezer at −20° C. for 20 days, no deposition of crystals was observed.

EXAMPLE B 1-(3,4-difluorophenyl)-4-(4-(4-pentylcyclohexyl)cyclo-hexyl)cyclohexyl)-2-Z-butene, hexyl)-2Z-butene (15%) of the compound of the present invention was mixed with the above liquid crystal composition ZLI-1132 and the physical properties of the resulting composition were measured. The results were as follows:
$C_P$(°C.)=68.3, $\Delta\epsilon$=10.2, $\epsilon\perp$=4.7, $\Delta n$=0.125, $\eta_{20}$=25.9, $V_{10}$=1.60.

Further, when this composition was allowed to stand in a freezer at −20° C. for 20 days, no deposition of crystals was observed.

The compound of the present invention has a particularly low viscosity and a high compatibility as compared with the prior liquid crystal materials, and is a novel compound having a broad mesomorphic temperature range.

While a liquid crystal compound of three rings generally has a suitable elastic constant ratio and is suitable as a material for a composition for STN, it has a high viscosity as compared with a compound of two rings. To improve this, a countermeasure such as using a viscosity-reducing agent is required. The compound of the present invention, particularly that having fluorine atom(s) for substituent(s) on the phenyl ring, has a relatively high elastic constant ratio while having a viscosity similar to that of the compound of two rings, and has a broad mesomorphic temperature range. Further, the compound of the present invention has a suitable optical anisotropy value, and can be used stably without any trouble under the ordinal environment. Thus, the characteristics of the liquid crystal composition can be improved by containing the compound of the present invention therein.

What we claim is:

1. A cis-1,4-substituted 2-butene derivative expressed by the formula (I)

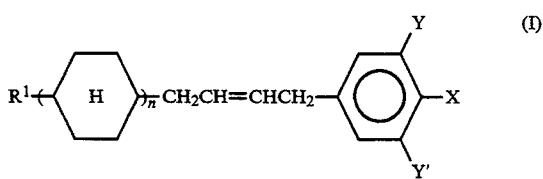

wherein $R^1$ represents an alkyl group of 1 to 10 carbon atoms; n represents 1 or 2; X represents a hydrogen atom, an alkyl group of 1 to 5 carbon atoms, a halogen atom, a cyano group, an alkoxy group of 1 to 5 carbon atoms, a methyl group substituted by 1 to 3 halogen atom(s) or a trihalomethoxy group; and Y and Y' each independently represent a hydrogen atom or a halogen atom.

2. A cis-1,4-substituted 2-butene derivative according to claim 1, wherein X represents a fluorine atom, Y and Y' represent a hydrogen atom or a fluorine atom, and n represents 1.

3. A cis-1,4-substituted 2-butene derivative according to claim 1, wherein X represents a cyano group, Y and Y' represent a hydrogen atom or a fluorine atom, and n represents 1.

4. A cis-1,4-substituted 2-butene derivative according to claim 1, wherein X represents a fluorine atom, Y and Y' represent a hydrogen atom or a fluorine atom, and n represents 2.

5. A cis-1,4-substituted 2-butene derivative according to claim 1, wherein X represents a cyano group, Y and Y' represent a hydrogen atom or a fluorine atom, and n represents 2.

6. A cis-1,4-substituted 2-butene derivative according to claim 1, wherein Y represents an alkyl group of 1 to 5 carbon atoms.

7. A liquid crystal composition comprising at least two components at least one of which is a cis-1,4-substituted 2-butene derivative as set forth in claim 1.

* * * * *